United States Patent [19]

Cook et al.

[11] Patent Number: 4,994,751

[45] Date of Patent: Feb. 19, 1991

[54] SYSTEM FOR ASSESSING LACHRYMAL FLUID CONTENT OF A SAMPLE PAD

[75] Inventors: Jerry W. Cook, 7400 NW. Whipple, Kansas City, Mo. 64152; Edward T. Fago, Jr., Kansas City, Mo.

[73] Assignee: Jerry W. Cook, Kansas City, Mo.

[21] Appl. No.: 393,223

[22] Filed: Aug. 14, 1989

[51] Int. Cl.$^5$ .................... G01R 27/26; G01N 31/00
[52] U.S. Cl. .................... 324/674; 324/690; 324/661; 422/82.02; 128/771
[58] Field of Search ............ 324/658, 663, 664, 667, 324/674, 681, 686, 689, 690, 692, 661; 128/760, 645, 745, 771, 734; 422/82.02; 436/150, 806; 435/817

[56] References Cited

U.S. PATENT DOCUMENTS

| | | | |
|---|---|---|---|
| 3,206,386 | 9/1965 | Kopito | 422/82.02 X |
| 3,753,099 | 8/1973 | Kleinberg et al. | 324/61 QS |
| 4,584,522 | 4/1986 | Varela | 324/670 X |
| 4,881,025 | 11/1989 | Gregory | 324/690 X |

Primary Examiner—Kenneth Wieder
Assistant Examiner—Jack B. Harvey
Attorney, Agent, or Firm—Hovey, Williams, Timmons & Collins

[57] ABSTRACT

A system rapidly and accurately assesses the lachrymal fluid content in a person's eye which minimizes patient discomfort. The preferred system includes a fluid sampling device and an assessment device. The preferred sampling device includes a lachrymal fluid absorbent sample pad and a non-absorbent handle. The preferred assessment device includes a receiver for receiving a lachrymal fluid sample pad and includes a control circuit coupled with the receiver for determining the electrical capacitance of the pad which capacitance varies in accordance with variations in lachrymal fluid content, and for producing an output correlated with the lachrymal fluid quantity in the pad.

11 Claims, 5 Drawing Sheets

SYSTEM FOR ASSESSING LACHRYMAL FLUID CONTENT OF A SAMPLE PAD

BACKGROUND OF THE INVENTION

1. Field of the Invention

The present invention concerns an accurate and rapid system for assessing lachrymal fluid content in a person's eye and which also minimizes patient discomfort. More particularly, the invention concerns a sampling device for taking a representative lachrymal fluid sample from a person's eye, and an assessment device which determines an electrical parameter, preferably capacitance, which varies in accordance with the lachrymal fluid content of the sampling device and produces an output correlated therewith, such being thereby correlated with the lachrymal fluid content of the person's eye from which the sample was taken.

2. Background of the Prior Art

The lachrymal fluid content of a person's eye has a bearing on general eye health, and in particular, is a factor in whether a person can wear contact lenses. That is,, to say, if a person's eyes produce insufficient lachrymal fluid, that is tears, then contact lenses are contra-indicated because the potential for irritation and discomfort.

Those skilled in the art are familiar with the so-called Shirmer test for assessing the lachrymal fluid content of a person's eye. The Shirmer test comprises an elongated, fluid absorbent sample member made of filter paper. One end of the member is inserted under the lower eye lid of the eye being checked with the other end protruding. The sample member is retained in the eye for five minutes in order to allow the member to absorb a sufficient sample amount. The distance the lachrymal fluid migrates or "wicks" along the member toward the exposed end provides an indication of the lachrymal fluid content of the person's eye.

As those skilled in the art appreciate, the Shermer test is not considered accurate because the relatively long term presence of the sampling member in a person's eye causes irritation and, in response, excess fluid production which distorts the results of the test. Because the test relies on wicking action, it also presents some inherent inaccuracies.

SUMMARY OF THE INVENTION

The present invention solves the prior art problems as outlined above. That is to say, the invention hereof provides an accurate and rapid system for assessing lachrymal fluid content in a person's eye in manner which minimizes patient discomfort.

Broadly speaking, the system hereof includes a sampling device and an assessment device. The sampling device includes a sample pad which is absorbent of lachrymal fluid at a predetermined known rate, and a handle portion which is non-absorbent of lachrymal fluid to prevent wicking therealong and used for placing the sample pad in substantially flush engagement with the patient's eye surface.

The preferred assessment device includes a receiver for receiving a lachrymal fluid sample pad such as that described above and an electrical circuit coupled with the receiver for determining an electrical parameter, preferably capacitance of the pad, and responsive thereto for producing an output correlated with the lachrymal fluid content of the sample pad and thereby correlated with the lachrymal fluid amount present in the person's eye from which the sample was taken.

In preferred forms, the receiver includes a pair of shiftable electrodes which define a sample pad receiving space therebetween. The preferred electrical circuit includes a microprocessor with an associated memory for storing correlation data which is used to correlate the output of the circuit with the electrical parameter. Other preferred aspects of the invention are discussed further hereinbelow.

BRIEF DESCRIPTION OF THE DRAWING FIGURES

DETAILED DESCRIPTION OF THE PREFERRED EMBODIMENT

Figure 1:
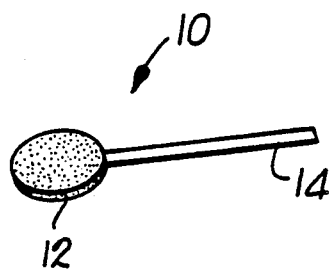
FIG. 1 is a perspective view of the preferred lachrymal fluid sampling device.

Referring initially to FIG. 1, preferred lachrymal fluid sampling device 10 includes disk-shaped sample pad 12 and elongated handle 14, one end of which is coupled with an edge of sample pad 12 to present the structure illustrated. Sample pad 12 is preferably composed of material absorbent of lachrymal fluid at a predetermined known rate. Such materials include polyvinylformal or, less preferred, Whatman 3 filter paper. Sample pad 12 preferably presents a circular, relatively flat, disk-shaped configuration presenting a known, predetermined surface area preferably selected from between 25 to 30 square millimeters in area.

Handle 14 is preferably composed of relatively thin, synthetic resin material which is non-absorbent of lachrymal fluid in order to prevent fluid migration or wicking therealong which has led to measurement inaccuracies in the prior art.

In use, handle 14 is grasped and one face of sample pad 12 placed in substantially total flush engagement with the sclera of a patient's eye for a predetermined sample time, preferably three seconds. The sample time is chosen to be long enough to absorb a representative lachrymal fluid sample but short enough so that the pad is removed before the patient physiologically responds with increased production of lachrymal fluid which has been a problem in the prior art. The preferred sample time of three seconds compared to five minutes in the prior art also minimizes patient discomfort.

As those skilled in the art will appreciate, the amount of lachrymal fluid present in a typical patient eye is extremely small, in the range of 5 microliters, and the sample quantity absorbed by sample pad 12 is even smaller, in the range of 0.5 microliters. Accordingly, and in order to provide uniform and repeatable results, it is preferred that the dimensions of sample pad 12 be precisely controlled during the manufacture to provide uniformity in dimensions and uniformity in the structure of the sample pad material itself. It is also preferred that the sample time also be precisely controlled so that the only variable in the sampling process is the lachrymal fluid present in the patient's eye. As explained further hereinbelow, the preferred assessment device provides means for compensating for relative humidity.

Figure 2:
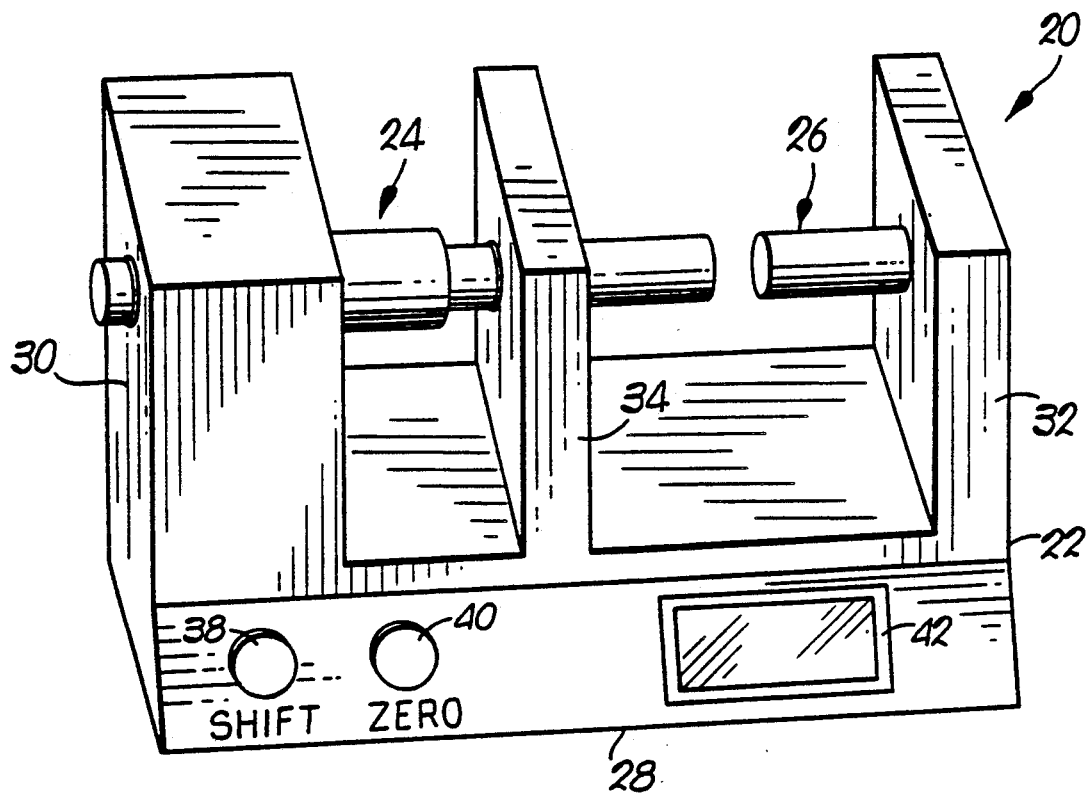
FIG. 2 is a perspective view of the preferred assessment device showing the shiftable electrode in the retracted position.

FIG. 2 presents a perspective view of preferred assessment device 20 which is used to determine an electrical parameter, preferably capacitance, which varies in accordance with variations in the quantity of lachrymal fluid present in sample pad 12. As illustrated, assessment device 20 includes housing 22, axially shiftable electrode 24, and fixed electrode 26.

Housing 22 is preferably composed of stainless steel or synthetic resin material and includes base 28, shiftable electrode support member 30, fixed electrode support member 32, and upstanding intermediate support member 34.

Base 28 encloses control circuit 36 (FIGS. 3–5) and includes shift switch 38 for electrically actuating shiftable electrode 24 leftwardly as shown in FIG. 2, zero switch 40 which is used to zero circuit 36 as explained further hereinbelow, and liquid crystal display 42.

Shiftable electrode 24 presents a generally cylindrical configuration and includes central section 44 presenting stop shoulder 46, smaller diameter electrode section 48 extending rightwardly (as viewed in FIG. 2) from stop shoulder 46 and through intermediate support 34 toward fixed electrode 26, and outboard section 50 extending leftwardly from central section 44. As illustrated, sections 44, 48, and 50 are axially aligned. Housing support member 30 encloses a conventional, +10 v.d.c., solenoid coil (not shown) which surrounds that portion of shiftable electrode 24 therein and is electrically connected with shift switch 38 for electromagnetic shifting of electrode 24 to the retracted position as shown in FIG. 2. Housing support member 30 also encloses conventional biasing spring (not shown) which abuts the leftward shoulder (not shown) of central section 44 in order to bias electrode 24 rightwardly to the engaged position. FIG. 2 illustrates shiftable electrode 24 in the shifted or retracted position as actuated by activation of shift switch 38.

Fixed electrode 26 is threadably coupled with support member 32 to allow axial adjustment thereof. Electrodes 24,26 define sample pad receiving space 52 therebetween. When deenergized, the biasing spring shifts electrode 24 rightwardly until stop shoulder 46 abuts the leftward face of intermediate support 34, thus assuring return of electrode 24 to the same position each time in order to present precisely controlled and uniform receiving space 52.

In the unretracted position, space 52 is narrow enough to slightly compress a sample pad received therein in order to hold it in place. The dimension of receiving space 52 can be adjusted very precisely by means of the threaded connection of fixed electrode 26 with housing support member 32.

When using the preferred sample device 10, the user holds device 10 by grasping handle 14 in order to place sample pad 12 in space 52 while activating shift switch 38 to retract electrode 24. After pad 12 is in placed in space 52, switch 38 is released and electrode 24 returns to the engaged position to hold sample pad 12 against fixed electrode 26. Sample handle 14 can then be released.

Figure 4:
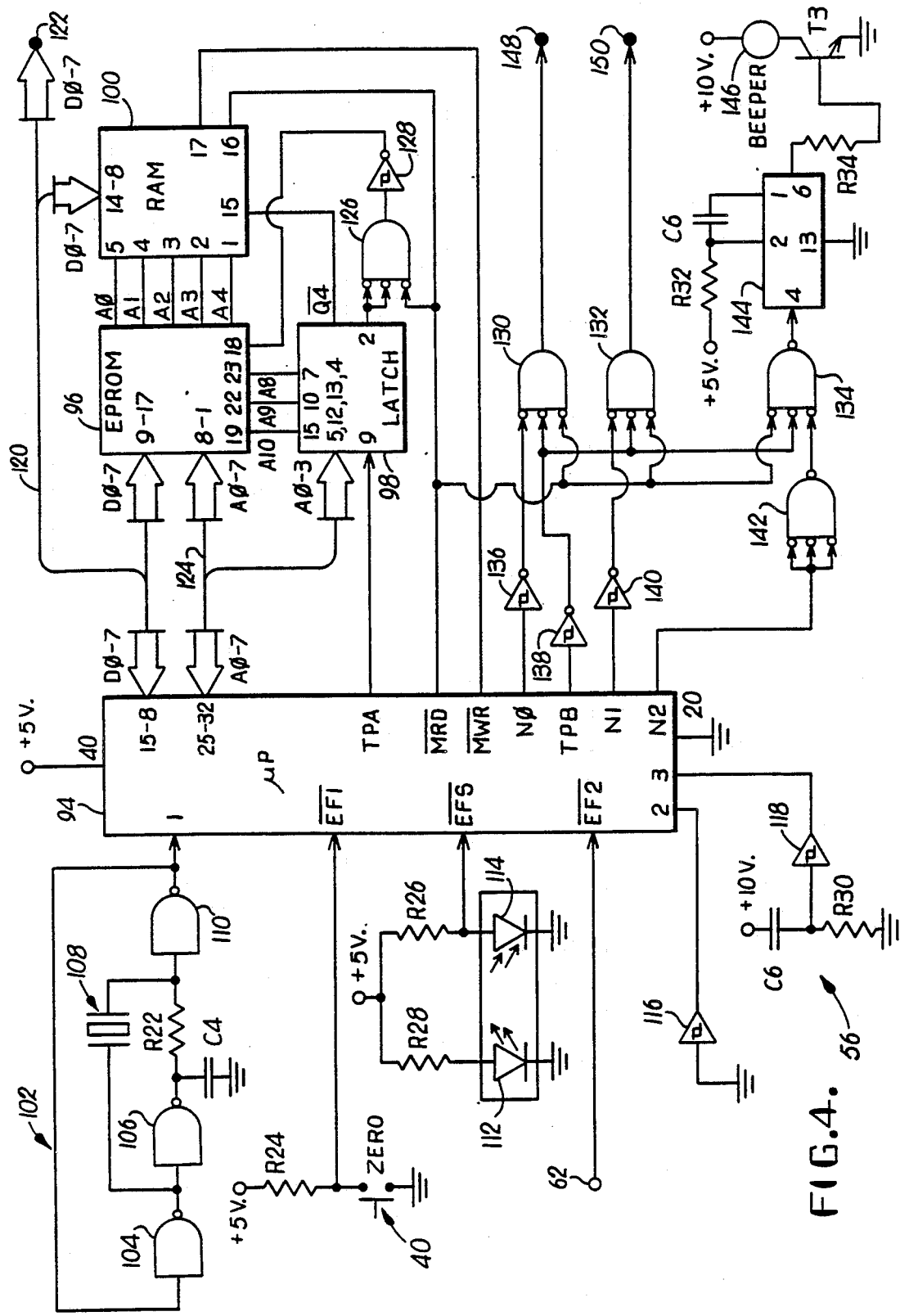
FIG. 4 is an electrical schematic diagram of the signal processing circuit of the assessment device.
Figure 5:
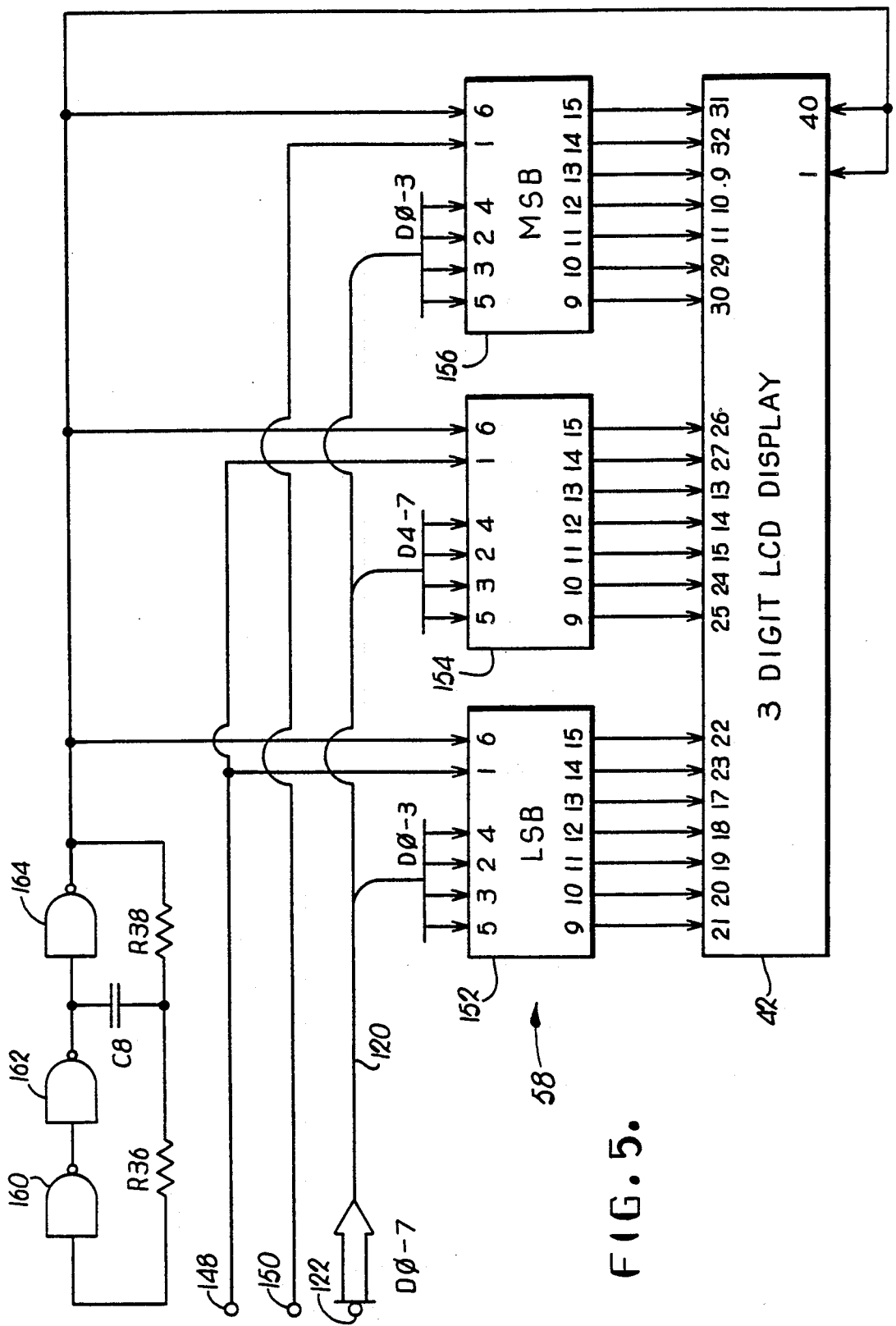
FIG. 5 is an electrical schematic diagram of the display circuit of the assessment device.

Control circuit 36 includes capacitance circuit 54 (FIG. 3), signal processing circuit 56 (FIG. 4), and display circuit 58 (FIG. 5). Control circuit 36 also includes a conventional power supply well known to those skilled in the art for receiving operating power from a conventional 120 v.a.c. outlet or batteries in order to provide required operating voltages at +10 and +5 v.d.c., and to supply operating power to the solenoid coil for shifting electrode 24.

Figure 3:
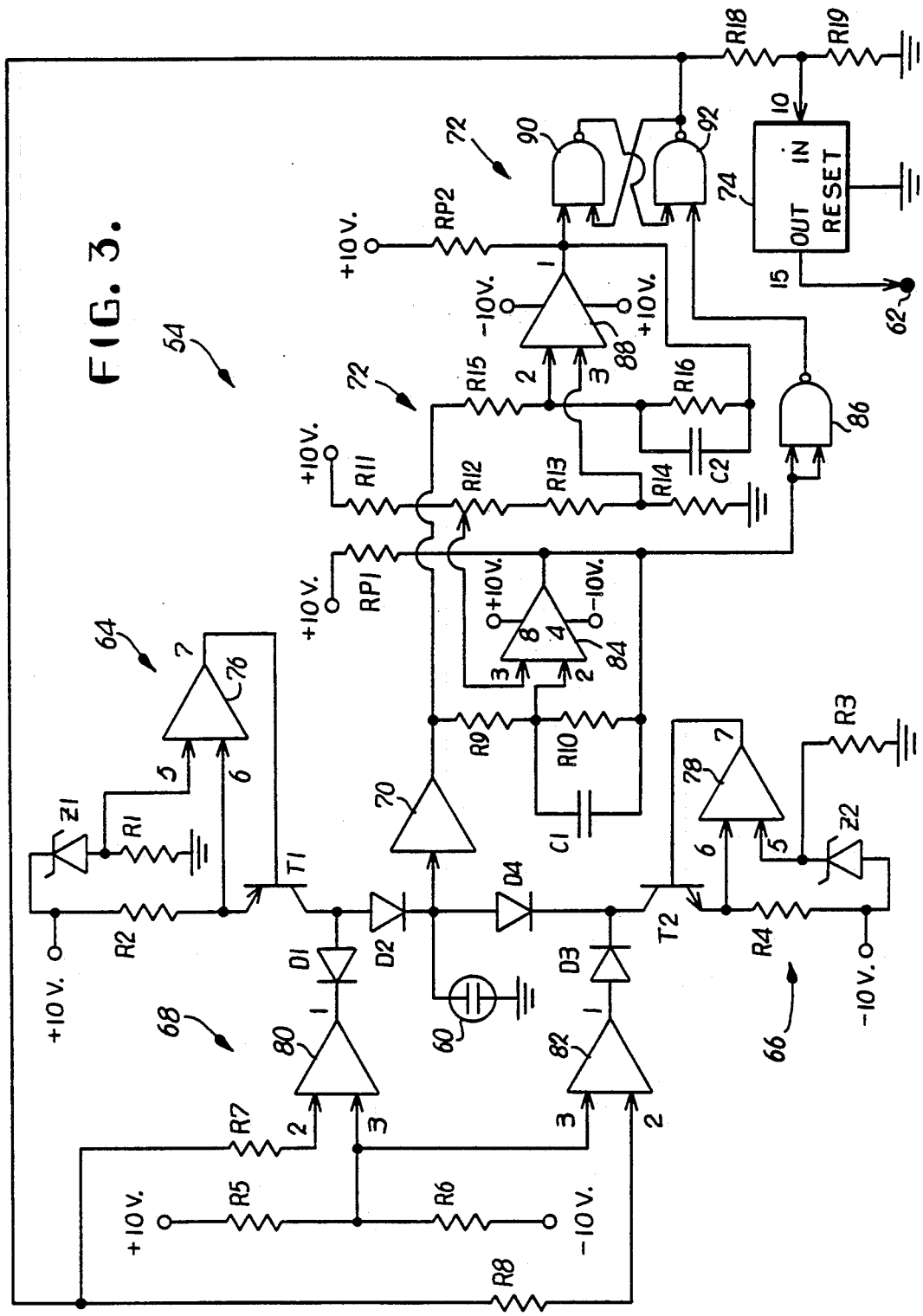
FIG. 3 is an electrical schematic diagram of the capacitance determining circuit of the assessment device of FIG. 1.

Capacitance circuit 54 (FIG. 3) determines the capacitance between electrodes 24,26 which represented in FIG. 3 as capacitor 60. In general, circuit 54 determines this capacitance, which varies in accordance with the amount of lachrymal fluid present in a sample, and provides a capacitance signal at output terminal 62. This signal is in the form of a square wave the frequency of which varies in accordance with the capacitance of capacitor 60.

As those skilled in the art will appreciate, a sample pad with lachrymal fluid present therein presents other parameters, such as resistance, which could be used for determining the amount of lachrymal fluid present in the sample pad and converted into a suitable and useable signal. In the preferred environment, however, determination of sample pad capacitance is preferred as providing the most accurate and repeatable parameter.

Capacitance circuit 54 broadly includes positive constant current source 64, negative constant current source 66, switching circuit 68, isolation amplifier 70, voltage comparator network 72, and output frequency divider 74.

Positive constant current source 64 is used to supply a charging current to capacitor 60 and includes Zener diode Z1 (type 1N827A) the cathode of which is coupled to supply voltage at +10 v.d.c. The anode of diode is coupled to one side of grounded resistor R1 (1.3K ohms) and to terminal 5 of comparator 76 as a reference voltage.

The output from comparator 76 is connected to the base of NPN transistor T1 (type 2N3906) the collector of which is connected to comparator terminal 6 and to one side of current limiting resistor R2 (1.0M ohms), the other side of which is connected to supply voltage. With this arrangement, the emitter of transistor T1 provides a constant current output at about 6 microamps.

Negative constant current source 66 is similarly configured and includes Zener diode Z2 (type 1N827A), the anode of which is connected to negative supply voltage at −10 v.d.c. The cathode of diode Z1 is connected to one side of grounded resistor R3 (1.3K ohms) and to terminal 5 of comparator 78 (type MC1458). The output of comparator 78 is connected to the base of PNP transistor T2 (type 2N3904), the emitter of which is connected to terminal 6 of comparator 78, and to one side of resistor R4 (1.0M ohms), the other side of which is connected to negative supply voltage. With this configuration, the collector of transistor T2 provides a constant current sink, also at 6 micro-amps.

Switching circuit 68 functions to alternately switch current sources 64 and 66 to alternately charge and discharge capacitor 60. Switching circuit 68 includes positive switching comparator 80 (type MC1458) which receives a reference input at terminal 3 from the juncture of resistor R5 (150K ohms), the other side of which is connected to positive supply voltage, and of resistor R6 (220K ohms), the other side of which is connected to negative supply voltage. Resistors R5 and R6 thereby form a voltage divider network to supply reference voltage to comparator 80. The other input at terminal 2 of comparator 80 is received by way of current limiting resistor R7 (20K ohms) from voltage comparator network 72. The output of comparator 80 is connected to the cathode of diode D1, the anode of which is connected to the emitter of transistor T1, and also to the anode of diode D2.

When the input voltage at terminal 2 of comparator 80 is logic low (0 volts) the output therefrom is logic high at +10 v.d.c. which reverse biases diode D1 and diverts the positive current flow through diode D2, the cathode of which is connected to capacitor 60, in order to charge capacitor 60. When the input to comparator terminal 2 is high, the output terminal sinks current and thereby diverts the positive constant current from current source 64 through diode D1.

Switching circuit 68 also includes negative switching comparator 82 which receives a reference voltage at terminal 3 thereof in common with the reference voltage on comparator 80. Comparator 82 receives feedback at terminal 2 thereof from network 72 by way of resistor R8 (20K ohms). The output from comparator 82 is connected to the anode of diode D3, the cathode of which is connected to the collector of transistor T2, and to the cathode of diode D4. The anode of diode D4 is connected to capacitor 60 and to the cathode of diode D2.

When the feedback voltage at terminal 2 of comparator 82 is logic low, the output from comparator 82 is logic high at +10 v.d.c. which forwardly biases diode D3 to provide current to negative source 66 in order to allow capacitor 60 to charge.

When comparator terminal 2 is logic high, the output of comparator 82 is logic low at −10 v.d.c. which reverse biases diode D3 and allows source 66 to sink current and thereby discharge capacitor 60 by way of diode D4.

With this arrangement, switching circuit 68 alternately switches current sources 64 and 66 to repetitively charge and discharge capacitor 60 according to the feedback from voltage comparator network 72. This feedback, as explained further hereinbelow, toggles between logic high at +10 v.d.c. and logic low at 0 v.d.c.

Capacitor 60 is also connected to and provides input to isolation comparator 70 (type LM310) which isolates comparator 60 from voltage comparator network 72.

Voltage comparator network 72 is configured to sense the voltage on capacitor 60 by way of isolation comparator 70 and, specifically, is designed to toggle the voltage on capacitor 60 between +0.4 v.d.c. and +4.0 v.d.c. The time frequency for this to occur depends upon the capacitance of capacitor 60 and thereby is a determination of the capacitance.

The output from comparator 70 is connected to one side of resistor R9 (1.2K ohms), the other side of which is connected to one side of capacitor C1 (500 p.F.), to one side of resistor R10 (91K ohms), and to terminal 2 of high toggle voltage comparator 84 (type LM311). Reference voltage to terminal 3 of comparator 84 is supplied by the voltage divider network composed of series connected resistors R11 (22K ohms), potentiometer resistor R12 (2K ohms full range), R13 (4.7K ohms), and R14 (270 ohms). As shown, one side of resistor R11 is connected to positive supply voltage and one side of resistor R14 is connected to ground. Reference voltage from the voltage tap of resistor R12 is supplied to terminal 3 of comparator 84. The output from comparator 84 is connected to the other sides of resistor R10 and capacitor C1 to both inputs of NAND 86, and to one side of pull up resistor RP1 (22K ohms), the other side of which is connected to supply voltage at +10 v.d.c.

The output from isolation comparator 70 is also connected to one side of current limiting resistor R15 (1.2K ohms), the other side of which supplies input voltage to terminal 2 of low toggle comparator 88, to one side of capacitor C2 (500 p.F.), and to one side of resistor R16 (91K ohms).

Reference voltage to terminal 3 of comparator 88 is supplied from the juncture of resistors R13 and R14. The output from comparator 88 is connected to the other sides of capacitor C2 and resistor R16, to one side of pull up resistor RP2 (22K ohms), the other side of which is connected to positive supply voltage, and to the input of NAND 90.

The output from NAND 90 is provided as one input to NAND 92, the output of which supplies the other input to NAND 90 and also supplies the toggle switching feedback to switching comparators 80 and 92 by way of resistors R7 and R8 respectively. The other input to NAND 92 is supplied from NAND 86.

Upon start-up, the inputs to terminals 2 of comparators 80 and 82 are logic low. As a result, comparator 80 provides an output at +10 v.d.c. to reverse bias diode D1 which in turn diverts positive constant current to capacitor 60 for charging. At the same time, comparator 82 provides an output at +10 v.d.c. to forward bias diode D3 and thereby supply negative constant current to circuit 66. During the voltage rise on capacitor 60, the output from high toggle comparator 84 is logic low and the output from low toggle comparator 88 is logic high.

When the voltage on capacitor 60 reaches approximately 4.0 v.d.c., high toggle comparator 84 switches state to logic high which is inverted by NAND 86 to provide a logic low signal to NAND 92 which changes state to provide a logic high output to switching circuit 68. The outputs from switching comparators 80,82 then switch state to −10 v.d.c. Comparator 80 then sinks current through diode D1 from positive current source 64. The output from comparator 82 provides reverse bias to diode D3 which allows capacitor 60 to discharge through diode D4 to negative current source 66.

When the voltage on capacitor 60 drops to about +0.4 v.d.c., the output from low toggle comparator 88 switches state to provide a logic low output to NAND 90 which toggles NAND 92 to change state to provide an output at logic low. This allows positive current source 64 to again supply current by way of diode D2 to capacitor 60. Thus, the output from voltage comparator network 72 is a square wave which toggles between 0 and +10 v.d.c.

The output from network 72 is also provided to series connected resistors R18 and R19 (both 11K ohms). One side resistor R19 is connected to ground as shown, and the juncture between resistors R18,R19 is connected to input terminal 10 of frequency divider 74 (type CD4020). Frequency divider 74 divides the input frequency by a factor of 2048 and provides a square wave output which toggles between 0 and +5 v.d.c. at output terminal 62. Thus, the output at terminal 62 is a capacitance signal in the form of a square wave, the frequency of which is correlated with the capacitance of capacitor 60, that is, of the capacitance between electrodes 24 and 26 which varies as a function of the amount of lachrymal fluid present in the sample pad therebetween.

FIG. 4 illustrates signal processing circuit 56 which includes a microprocessor 94 (type CDP1802), eraseable, programmable read-only-memory 96 (EPROM, type 2716), address latch 98 (type CD40175), and random-access-memory 100 (RAM, type CDP1824), among other components. Microprocessor 94 receives supply power at +5 v.d.c. at pin 40. Ground is connected to pin 20. Input clock signals are received at terminal 1 at 1 megahertz which is provided by oscillator circuit 102. This circuit includes NAND 104, the output of which is connected to the input of NAND 106 and to one side of crystal 108 (one megahertz). The output from NAND 106 is connected to one side of grounded capacitor C4 (500 p.F.) and to one side of resistor R22 (1.2K ohms). The other side of resistor R22 is connected to the other side of crystal 108 and to the input of NAND 110. The output from NAND 110 is connected to the input of NAND 104 and to terminal 1 of microprocessor 94. As so configured, oscillator circuit 102 provides the required clock signals at 1 megahertz.

Microprocessor 94 receives a zeroing input at terminal $\overline{EF1}$ which is connected to the juncture between resistor R24 (22K ohms) and normally open zero switch 40 (see also FIG. 2). The other side of resistor R24 is connected to supply voltage, and the other side of switch 40 is connected to ground as shown. Switch 40 is used to provide a "zero" indication to microprocessor 94 when an unused sample pad is placed between electrodes 24,26. This provides a zero level which compensates for relative humidity and for variations between the batches of sample pads 12.

Input to microprocessor terminal $\overline{EF3}$ is a signal indicating that a sample pad is present between electrodes 24,26. The signal is produced by providing a light emitting diode (LED) 112 and a light receiving diode 114 respectively disposed on opposed sides of receiving space 52. When a sample pad is present between electrodes 24,26, the light output from LED 112 is blocked and diode 114 no longer conducts. This allows a voltage rise at the anode thereof from supply voltage by way of pull-up resistor R26 (22K ohms). Power is supplied to the anode of LED 112 by way of current limiting resistor R28 (270 ohms). The cathodes of both diodes are connected to ground as shown.

Microprocessor 94 also receives inputs at terminal 2 thereof from Schmitt trigger 116 the input of which is connected to ground and at terminal 3 from the output of Schmitt trigger 118. The input to trigger 118 is connected to the juncture between capacitor C6 (1.0 u.F.) the other side of which is connected to +10 v.d.c. and resistor R30 (11K ohms), the other side of which is connected to ground.

Eight line data bias 120 includes lines D0–D7 connected to microprocessor terminals 15–8 respectively, EPROM terminals 9–17 respectively, RAM terminals 14–18 respectively, and to output terminals designated as 122.

Eight line address bus 124 includes lines A0–A7 connected to microprocessor terminals 25–32 respectively and EPROM terminals 8–1 respectively. Address lines A0–A3 are connected to latch terminals 5, 12, 13, and 4 respectively. As shown, additional address lines A10, 9, and 8 respectively interconnect latch terminals 15, 10, and 7 with EPROM terminals 19, 22, and 23. Additionally, lines A0–A4 interconnect EPROM 96 with RAM terminals 5–1 respectively.

Microprocessor 94 also provides an output at terminal TPA to terminal 9 of latch 98. Latch 98 terminal 2 is connected to two of the inverting input terminals of NAND 126, the output of which is connected by way of inverter 128 to EPROM terminal 18.

Microprocessor terminal $\overline{MRD}$ is connected to AND 126, RAM terminal 16, NAND 130, to NAND 132, and to NAND 134. Microprocessor terminal $\overline{MWR}$ is connected to RAM terminal 17.

Terminal N0 of microprocessor 94 provides an output by way of inverter 136 to NAND 130. Another output is provided at terminal TPB by way of inverter 138 to NAND 130, NAND 132, and NAND 134. Microprocessor output terminal N1 is connected by way of inverter 140 to NAND 132 and terminal N2 is provided as all three inputs to NAND 142, the output of which is connected to NAND 134.

The output from NAND 134 is connected to terminal 4 of beeper control unit 144 (type CD4098). Terminal 2 of unit 144 is connected to one side of resistor R32 (1M ohms), the other side of which is connected to supply voltage at +5 v.d.c., and to one side of capacitor C6 (1 u.F.), the other side of which is connected to unit terminal 1. Control unit terminal 13 is connected to ground as shown. Control unit 144 provides an output at terminal 6 thereof by way of resistor R34 (5K ohms) to the base of transistor T3. The emitter of transistor T3 is connected to ground and the collector is connected to one side of beeper 146 (Mallory brand Minilert), the other side of which is connected to supply voltage at +10 v.d.c.

Processing circuit 56 receives the squarewave input at terminal 62 from capacitance circuit 54 which is provided at input to microprocessor terminal $\overline{EF2}$. In response, as explained further hereinbelow in connection with the operating program, processing circuit 56 produces respective outputs at data output terminals 122, output terminal 148 connected to the output of NAND 130, and output terminal 150 provided as the output from NAND 132. These terminals present the output from control circuit 56 to display circuit 58 (FIG. 5).

In operation, a logic low output at microprocessor terminal $\overline{MRD}$ and logic high outputs at microprocessor terminals N0 and TPB provide a logic high output at terminal 148 which enables writing data, by way of data bus 120 at terminal 122, for the two most significant digits of display circuit 58.

A logic low signal at microprocessor terminal $\overline{MWR}$ and logic high signals at terminals TPB and N1 result in a logic high signal at output terminal 150 which enables data writing by way of output terminal 122 for the least significant digit of the display.

In order to activate beeper 146, microprocessor 94 produces a logic low signal at terminal $\overline{MRD}$ to AND 134, a logic high signal at terminal TPB by way of inverter 138 to NAND 134, and a logic low signal at terminal N2 to NAND 142 and then to NAND 134. With these three inputs at NAND 134, its output goes logic low to beeper control unit 144 which activates unit output terminal 6 by way of resistor R34 to the base of transistor T3 which then conducts to energize beeper 146.

FIG. 5 is an electrical schematic illustration of display circuit 58 including display 42 which is supplied by least significant bit latch/decoder 152, latch/decoder 154, and most significant bit latch/decoder 156, all three of which are type CD4056. Display circuit 58 receives display data over data bus 120 by way of terminal 122 of which data lines D0–D3 are connected to decoders 152 and 156, and data lines D4–D7 are connected to decoder 154 at the terminals shown. Decoders 152 and 154 receive logic high enabling signals at respective terminals 1 from processing circuit 56 by way of terminal 148. Similarly, decoder 156 receives an enable signal at terminal 1 thereof by way of terminal 150.

Oscillator circuit 158 is configured to provide squarewave signals at 100 hertz in order to alternate the electric field applied to the liquid crystals at that frequency as conventionally required in LCD displays. Oscillator circuit 158 includes NAND 160 the input to which is connected to one side of resistor R36 (47K ohms) and the output of which is provided as input to NAND 162. The output from NAND 162 is connected to one side of capacitor C8 (0.1 u.F.) and as input to NAND 164. The output from NAND 164 provides the required 100 hertz squarewave signals and is connected to respective terminals 6 of decoders 152–156, to terminals 1 and 40 of display 42, and to one side of resistor R38 (47K ohms). The other side of resistor R38 is connected to the other sides of capacitor C8 and resistor R36.

In operation, an enable signal by way of terminal 148 to latch/decoders 152 and 154 enables them to latch the data on data bus 120. Similarly, an enable signal at terminal 150 enables latch/decoder to latch the data on data lines D0–3. The latch data is then decoded and displayed to the respective segments of display 42 by way of the lines and terminals shown in FIG. 5.

Figure 6:
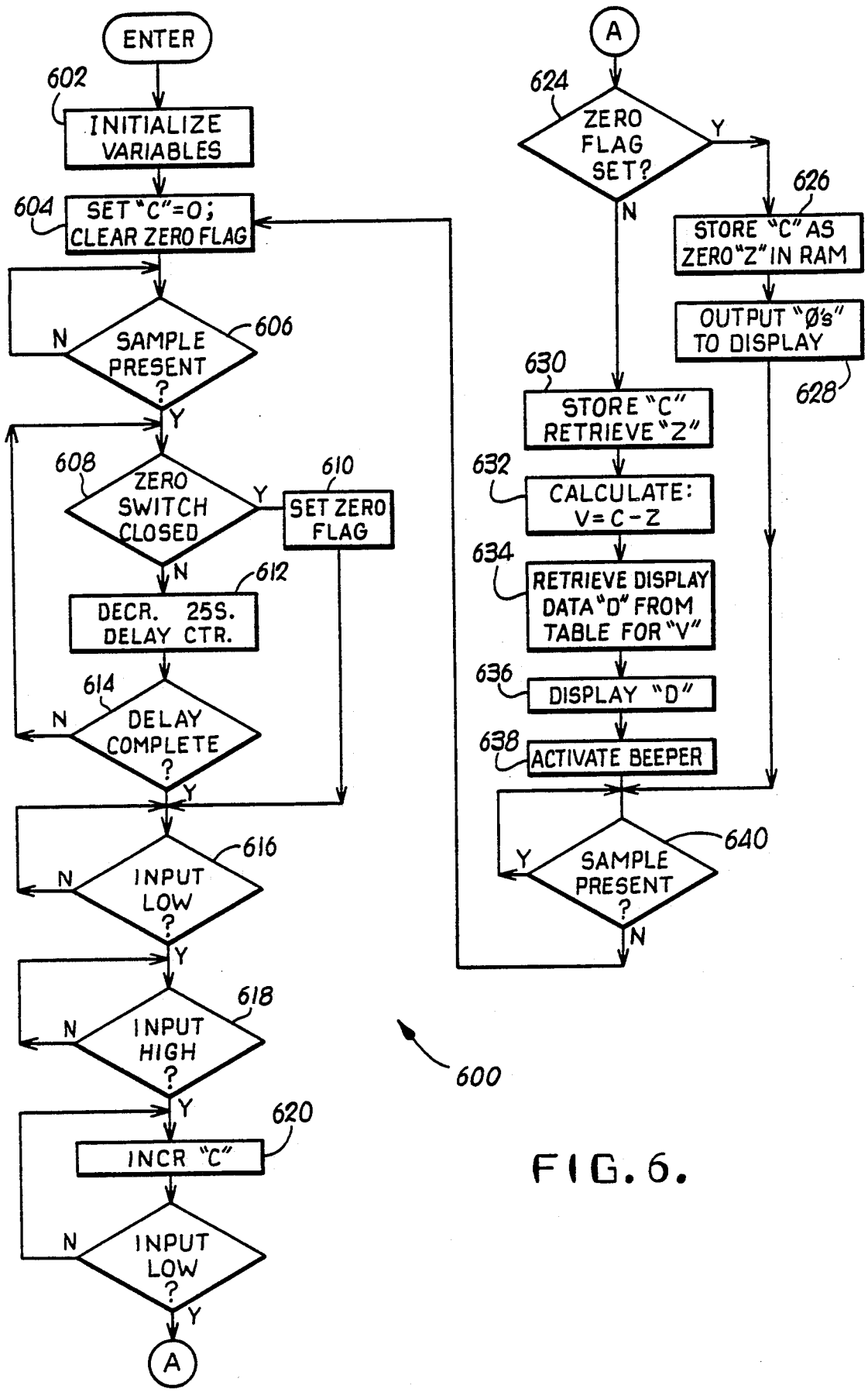
FIG. 6 is a computer program flowchart of the operating program for operating the assessment device.

FIG. 6 is a computer program flowchart illustrating the operating program 600 for operating assessment device 20 and in particular, for operating microprocessor 94. The program is stored in EPROM 96 and is preferably written in machine code.

The program enters at step 602 which initializes the hardware and software variables on power up. The program then moves to step 604 which sets the variable "C" equal to zero and clears a software "zero" flag.

The program then moves to step 606 which reads the input at microprocessor terminal $\overline{EF3}$ (FIG. 4) to determine if a sample pad is present between electrodes 24 and 26. That is to say, the presence of a sample pad which blocks the light transmission from diode 112 to diode 114 results in a logic high input at terminal $\overline{EFS}$ indicative of the presence of a sample pad. The program loops through step 606 in a standby mode until a sample is present.

When a sample is present, the answer in step 606 is yes and the program moves to step 608 which asks whether zero switch 40 is closed. If the answer in step 608 is yes, indicating that the zero switch is closed, the program moves to step 610 which sets the "zero" flag. If the answer in step 608 is no, the program moves to step 612 to decrement a twenty-five second delay counter which ensures that capacitance circuit 54 has time to stabilize before a reading is taken. After decrementing the delay counter one unit, the program moves to step 614 which asks whether the delay is complete, that is, whether the delay counter is decremented to zero. If no, the program loops back to step 608 and continues to loop through steps 612,614 until the delay is complete.

When the delay is complete in step 614, or after step 610, the program moves to step 616 which asks whether the input to microprocessor terminal $\overline{EF2}$ from capacitance circuit 54 is logic low. If no, the program continues to loop through step 616 until the answer is yes, at which point the program moves to step 618 which asks whether the input from capacitor circuit 54 is logic high. If no, the program continues to loop through step 618 until the answer is yes. Steps 616 and 618 ensure that the program marks the beginning of the logic high portion of the output squarewave provided from capacitance circuit 54 to microprocessor circuit 56.

When the answer in step 618 is yes, indicating the beginning portion of the logic high signal, the program moves to step 620 which increments counter "C" after which the program moves to step 622 which asks whether the squarewave signal from capacitance circuit 54 has changed state to logic low. If no, the program loops back to step 620 to again increment counter C. The program continues to loop through step 620 and 622 at the microprocessor clock rate as long as the capacitance circuit squarewave signal is high. In this way, counter "C" increments to a value representative of the time length of the positive portion of the squarewave signal. This in turn provides a value representative of the capacitance between electrodes 24 and 26. If a sample pad placed between electrodes 24 and 26 is a "dry" pad representing a "zero" level, then the final value of counter "C" represents the zero value.

When the input of the squarewave signal finally changes state to logic low, the program moves to step 624 which asks whether the zero flag is set, which may have been set in step 610. If yes, indicating that a dry sample pad for calibration purposes is in place, the program moves to step 626 to store the value of counter "C" as zero value "Z". This value is stored in RAM 100. The program then moves to step 628 to output all "zeroes" to display circuit 58.

If the answer in step 624 is no, the program moves to step 630 to store the value of counter "C" as then existing, and to retrieve the previously stored zero value "Z". The program then moves to step 622 to calculate the difference between the current counter "C" value and the zero "Z" value accordingly to the formula as shown to produce the value "V".

The program then moves to step 634 to retrieve from memory the appropriate data "D" for the value of "V" calculated in step 632. In other words, a look-up table is stored in memory in order to produce an output in the form of data "D" for display which is correlated with the value of "V", which in turn is correlated with the value of capacitance between electrodes 24,26, and which is further correlated with the amount of lachrymal fluid present in the sample pad being assessed.

The digits displayed on display panel 42 in response to data "D" are appropriately chosen to be meaningful to the operator of assessment device 20. For example, the displayed digits could represent a statistical variation from the norm as empirically statistically derived by sampling a large number of patients. For example, a display of 50 would indicate a statistically normal amount of lachrymal fluid present in a sample pad. Similarly, a reading of 95 might indicate a percentile of excessive lachrymal fluid. That is to say, data "D" would produce an output reading of 95 when the value "V" indicates a quantitive lachrymal fluid greater than 95% of the data base samples. Similarly, data "D" might be chosen to display "5" when the value of "V" indicates the sample a very minimal amount of lachrymal fluid as the fifth percantile.

After step 634, the program moves to step 636 to output the appropriate data by way of data bus 120 and the appropriate enabling signals by way of terminals 148 or 150 to display circuit 58 in order to produce a display in accordance therewith. The program then moves to step 638 to activate beeper 146 for a predetermined amount of time in order to alert the operator of assessment device 20 that the analysis is complete. The program then moves to step 640 which asks whether a sample is still present between electrodes 24,26. If yes, the program continues to loop through step 640 until the sample which has already been analyzed is removed. When the answer in step 640 is no, the program loops back to step 604 and is ready for the next sample.

As those skilled in the art will appreciate, the present invention encompasses many variations in the exemplary and preferred embodiment described herein. For example, sample pad 12 can present a rectangular shape or geometrical shape other than the preferred circular. Additionally, while the assessment device is preferably configured to determine the capacitance of a sample pad, the sample pad also presents other parameters, such as resistance, which can be determined and the information processed electronically. As a further example, control circuit 36 could be configured totally in hardware such as with a semiconductor chip without using a microprocessor and associated program, although such is preferred for economy and flexibility in the change of operation. Finally, while the preferred output of the assessment device is the form of a digital display using liquid crystals, other outputs may be used such as analog meters.

Having thus described the preferred embodiments of the present invention, the following is claimed as new and desired to be secured by Letters Patent:

1. A lachrymal fluid assessment device comprising:
   receiving means including a pair of electrodes for receiving a sample pad therebetween with the sample pad having an unknown quantity of lachrymal fluid present therein, and for presenting the sample pad for determination of the capacitance thereof, said unknown quantity being a representative sample of lachrymal fluid present in a person's eye, said capacitance being representative of said unknown quantity; and
   circuit means operably coupled with said receiving means for determining said capacitance, for producing a capacitance signal representative of said capacitance, and responsive thereof for producing an output correlated with said unknown quantity of lachrymal fluid present in the sample pad, said circuit means including processing circuit means responsive to said capacitance signal for producing said output;
   said processing circuit means including memory means for storing data correlating said output with said capacitance signal and thereby with said unknown quantity and with the amount of lachrymal fluid present in the person's eye.

2. An assessment device as set forth in claim 1, said receiving means including a pair of spaced electrodes defining a sample pad receiving space therebetween, said circuit means including capacitance determining means for determining the capacitance between said electrodes.

3. The assessment device as set forth in claim 2, said receiving means further including means shiftably mounting said electrodes in a biased, relatively shiftable relationship toward one another and including means for selectively altering the spacing between said electrodes in order to hold a sample pad having a predetermined width therebetween.

4. The assessment device as set forth in claim 1 said processing circuit means including a microprocessor.

5. The assessment device as set forth in claim 1, said circuit means including means for producing said capacitance signal as a frequency variable signal which frequency varies in correlation with said capacitance.

6. The assessment device as set forth in claim 5, said circuit means including zeroing means for calibrating said circuit means using a sample pad without lachrymal fluid absorbed therein.

7. The assessment device as set forth in claim 1, further including display means coupled with said circuit means and responsive to said output for displaying a representation of said quantity of lachrymal fluid present in the sample pad.

8. The assessment device as set forth in claim 7, said display means including a liquid crystal digital display.

9. The assessment device as set forth in claim 7, said representation being in terms of a percentile.

10. The assessment device as set forth in claim 1, said receiving means further including detection means for detecting the presence of a sample pad therein.

11. The assessment device as set forth in claim 1, said data being stored in said memory means as a look-up table.

* * * * *